United States Patent
Howard

(10) Patent No.: US 11,490,851 B2
(45) Date of Patent: Nov. 8, 2022

(54) NEUROANALYTIC, NEURODIAGNOSTIC, AND THERAPEUTIC TOOLS

(71) Applicant: Newton Howard, Providence, RI (US)

(72) Inventor: Newton Howard, Providence, RI (US)

(*) Notice: Subject to any disclaimer, the term of this patent is extended or adjusted under 35 U.S.C. 154(b) by 163 days.

(21) Appl. No.: 15/458,179

(22) Filed: Mar. 14, 2017

(65) Prior Publication Data
US 2017/0258389 A1 Sep. 14, 2017

Related U.S. Application Data

(60) Provisional application No. 62/308,212, filed on Mar. 14, 2016.

(51) Int. Cl.
A61B 5/00 (2006.01)
G16H 20/00 (2018.01)
(Continued)

(52) U.S. Cl.
CPC ........ A61B 5/4076 (2013.01); A61B 5/02055 (2013.01); A61B 5/165 (2013.01);
(Continued)

(58) Field of Classification Search
CPC ... A61B 5/02055; A61B 5/0476; A61B 5/165; A61B 5/4076; A61B 5/4082; A61B 5/4088; A61B 5/6817; A61B 5/0022; A61B 5/021; A61B 5/02438; A61B 5/04001; A61B 5/0402; A61B 5/0478;
(Continued)

(56) References Cited

U.S. PATENT DOCUMENTS 5,862,273 A 1/1999 Pelletier
7,645,482 B2 1/2010 Burke
(Continued)

OTHER PUBLICATIONS

Alivisatos, A. P., Andrews, A. M., Boyden, E. S., Chun, M., Church, G. M., Deisseroth, K., et al. (2013). Nanotools for Neuroscience and Brain Activity Mapping. ACS nano, 7(3), 1850-1866.
(Continued)

*Primary Examiner* — Jonathan T Kuo
*Assistant Examiner* — Vynn V Huh
(74) *Attorney, Agent, or Firm* — Michael A. Schwartz

(57) ABSTRACT

Embodiments may provide multimodal diagnostic systems and methods for detecting neurological disorders, such as Alzheimer's disease (AD), Parkinson's disease (PD), depression, PTSD, schizophrenia, dementia and many others. For example, a system for monitoring brain activity may comprise a plurality of sensors, each adapted to monitor a physical or physiological parameter and output a signal representing the monitored physical or physiological parameter, wherein the plurality of sensors includes at least one sensor configured to monitor a brain activity parameter, a data collection device adapted to receive the plurality of signals from the plurality of sensors and to process the signals to form digital data representing the monitored physical or physiological parameters, and a data processing device adapted to process digital data representing the monitored physical or physiological parameters to determine presence of a neurological disorder or condition.

9 Claims, 6 Drawing Sheets

(51) Int. Cl.

| | | |
|---|---|---|
| A61B 5/04 | (2006.01) | |
| G06F 3/01 | (2006.01) | |
| A61B 5/0205 | (2006.01) | |
| A61B 5/16 | (2006.01) | |
| A61B 5/0476 | (2006.01) | |
| G16H 40/63 | (2018.01) | |
| G16H 40/67 | (2018.01) | |
| A61B 5/0478 | (2006.01) | |
| A61B 5/024 | (2006.01) | |
| A61B 5/08 | (2006.01) | |
| A61B 5/021 | (2006.01) | |
| A61B 5/11 | (2006.01) | |
| A61B 5/145 | (2006.01) | |
| G16H 50/20 | (2018.01) | |
| G16H 50/30 | (2018.01) | |
| A61B 5/0402 | (2006.01) | |
| A61B 5/24 | (2021.01) | |
| A61B 5/369 | (2021.01) | |
| A61B 5/291 | (2021.01) | |
| A61B 5/318 | (2021.01) | |

(52) U.S. Cl.
CPC .............. *A61B 5/24* (2021.01); *A61B 5/369* (2021.01); *A61B 5/4082* (2013.01); *A61B 5/4088* (2013.01); *A61B 5/6817* (2013.01); *A61B 5/6868* (2013.01); *A61B 5/7264* (2013.01); *G06F 3/015* (2013.01); *G16H 20/00* (2018.01); *A61B 5/0022* (2013.01); *A61B 5/021* (2013.01); *A61B 5/02438* (2013.01); *A61B 5/0816* (2013.01); *A61B 5/1116* (2013.01); *A61B 5/14542* (2013.01); *A61B 5/291* (2021.01); *A61B 5/318* (2021.01); *A61B 5/4094* (2013.01); *G16H 40/63* (2018.01); *G16H 40/67* (2018.01)

(58) Field of Classification Search
CPC . A61B 5/0816; A61B 5/1116; A61B 5/14542; A61B 5/4094; A61B 5/6868; A61B 5/7264; G06F 19/00; G06F 19/30; G06F 3/015

See application file for complete search history.

(56) References Cited

U.S. PATENT DOCUMENTS

| | | | |
|---|---|---|---|
| 7,718,224 B2 | 5/2010 | Burke | |
| 7,721,347 B2 | 5/2010 | Burke | |
| 7,816,906 B2 | 10/2010 | Kalburge | |
| 7,857,956 B2 | 12/2010 | Burke | |
| 7,858,454 B2 | 12/2010 | Kalburge | |
| 7,871,851 B2 | 1/2011 | Kalburge | |
| 8,039,870 B2 | 10/2011 | Burke | |
| 8,149,170 B2 | 4/2012 | Burke | |
| 8,380,902 B2 | 2/2013 | Howard | |
| 8,407,271 B2 | 3/2013 | Hurd | |
| 8,692,575 B2 | 4/2014 | Gershenfeld et al. | |
| 8,789,053 B2 | 7/2014 | Howard | |
| 9,907,496 B1* | 3/2018 | Okandan | A61B 5/1459 |
| 2006/0212097 A1* | 9/2006 | Varadan | A61B 5/031 607/62 |
| 2008/0091089 A1* | 4/2008 | Guillory | A61B 5/0478 600/301 |
| 2008/0146890 A1* | 6/2008 | LeBoeuf | A61B 5/0059 600/300 |
| 2011/0060377 A1 | 3/2011 | Howard | |
| 2012/0064493 A1 | 3/2012 | Howard | |
| 2013/0338526 A1* | 12/2013 | Howard | A61B 5/04004 600/544 |
| 2014/0331229 A1 | 11/2014 | Howard | |
| 2015/0313496 A1* | 11/2015 | Connor | A61B 5/0476 600/301 |
| 2017/0231597 A1 | 8/2017 | Howard | |
| 2017/0251985 A1 | 9/2017 | Howard | |

OTHER PUBLICATIONS

Antoniades, C. A., Buttery, P., FitzGerald, J. J., Barker, R. A., Carpenter, R. H., & Watts, C. (2012). Deep Brain Stimulation: Eye Movements Reveal Anomalous Effects of Electrode Placement and Stimulation. PloS one, 7(3), e32830.

Bai, J., Zhong, X., Jiang, S., Huang, Y., & Duan, X. (2010). Graphene Nanomesh. Nature nanotechnology, 5(3), 190-194.

Bar, M., Kassam, K. S., Ghuman, A. S., Boshyan, J., Schmid, A. M., Dale, A. M., et al. (2006). Top-Down Facilitation of Visual Recognition. Proceedings of the National Academy of Sciences of the United States of America, 103(2), 149-454.

Barwicz, T., Byun, H., Gan, F., Holzwarth, C., Popovic, M., Rakich, P., et al. (2007) Silicon Photonics for Compact, Energy-Efficient Interconnects [Invited], Journal of Optical Networking, 6(1), 63-73.

Bernstein, J. G., & Boyden, E S (2011) Optogenetic Tools for Analyzing the Neural Circuits of Behavior. Trends in cognitive sciences, 15(12), 592-600.

Bernstein, J. G., Han, X., Henninger, M. A., Ko, E. Y., Qian, X., Franzesi, G. T., et al. (2008). Prosthetic Systems for Therapeutic Optical Activation and Silencing of Genetically Targeted Neurons. Paper presented at the Biomedical Optics (BiOS) 2008.

Boyden, E. (2011). A History of Optogenetics: The Development of Tools for Controlling Brain Circuits with Light. F1000 Biology Reports 2011, 3:11 (doi: 10.3410/B3-11).

Boyden, E. S., Zhang, F., Bamberg, E., Nagel, G., & Deisseroth, K. (2005). Millisecond-Timescale, Genetically Targeted Optical Control of Neural Activity. Nature neuroscience, 8(9), 1263-1268.

Boyle, P. M., Entcheva, E., & Trayanova, N. A. (2014). See the Light: Can Optogenetics Restore Healthy Heartbeats? And, If It Can, Is It Really Worth the Effort? Expert review of cardiovascular therapy, 12(1), 17-20.

Bruggemann, A., Haarmann, C., Stengel, T., Vogel, M., Steindl, J., Mueller, M., et al. (2014). Automated Patch Clamping of 384 Cells at Once for Massively Parallel Ion Channel Screening. Biophysical Journal, 106(2), 132a.

Chow, B. Y., Han, X., Dobry, A. S., Qian, X., Chuong, A. S., Li, M., et al. (2010). High-Performance Genetically Targetable Optical Neural Silencing by Light-Driven Proton Pumps. Nature, 463(7277), 98-102.

Dalrymple, D., Gershenfeld, N., & Chen, K. (2008). Asynchronous Logic Automata. Paper presented at the Automata.

Deisseroth, K. (2011). Optogenetics. Nature methods, 8(1), 26-29.

Doroudchi, M. M., Greenberg, K. P., Liu, J., Silka, K. A., Boyden, E. S., Lockridge, J. A., et al. (2011). Virally Delivered Channelrhodopsin-2 Safely and Effectively Restores Visual Function in Multiple Mouse Models of Blindness. Molecular Therapy, 19(7), 1220-1229.

Fenno, L., Yizhar, O., & Deisseroth, K. (2011). The Development and Application of Optogenetics. Neuroscience, 34(1), 389.

Gerits, A., Farivar, R., Rosen, B. R., Wald, L. L., Boyden, E. S., & Vanduffel, W. (2012). Optogenetically Induced Behavioral and Functional Network Changes in Primates. Current Biology, 22(18), 1722-1726.

Gorelik, J., Gu, Y., Spohr, H. A., Shevchuk, A. L, Lab, M. J., Harding, S. E., et al. (2002). Ion Channels in Small Cells and Subcellular Structures Can Be Studied with a Smart Patch-Clamp System. Biophysical Journal, 83(6), 3296-3303.

Han, X., & Boyden, E. S. (2007). Multiple-Color Optical Activation, Silencing, and Desynchronization of Neural Activity, with Single-Spike Temporal Resolution. PloS one, 2(3), e299.

Han, X., Qian, X., Bernstein, J. G., Zhou, H.-h., Franzesi, G. T., Stern, P., et al. (2009). Millisecond-Timescale Optical Control of Neural Dynamics in the Nonhuman Primate Brain Neuron, 62(2), 191-198.

(56) References Cited

OTHER PUBLICATIONS

Howard, N. (2013). The Twin Hypotheses: Brain Code and the Fundamental Code Unit Springer Lecture Notes in Artificial Intelligence, MICAI 2013, In Press.
Howard, N. (2014). Approach to Study the Brain: Towards the Early Detection of Neurodegenerative Disease. Oxford University, Bodleian Library.
Howard, N. (2015). The Brain Language: Psychotrauma Spectrum Disorder and Cybernetic Detection of Disease Conditions and Comorbidities. Universite de Paris Descartes.
Howard, N., Bergmann, J., & Stein, J. (2013). Combined Modality of the Brain Code Approach for Early Detection and the Long-Term Monitoring of Neurodegenerative Processes. Frontiers Special Issue INCF Course Imaging the Brain at Different Scales.
Johansen, J. P., Diaz-Mataix, L., Hamanaka, H., Ozawa, T., Ycu, E., Koivumaa, J., et al. (2014). Hebbian and Neuromodulatory Mechanisms Interact to Trigger Associative Memory Formation. Proceedings of the National Academy of Sciences, 111(51), E5584-E5592.
Kringelbach, M. L., Jenkinson, N., Owen, S. L., & Aziz, T. Z. (2007). Translational Principles of Deep Brain Stimulation. Nature Reviews Neuroscience, 8(8), 623-635.
LaLumiere, R. T. (2011). A New Technique for Controlling the Brain: Optogenetics and Its Potential for Use in Research and the Clinic. Brain stimulation, 4(1), 1-6.
Liewald, J. F., Brauner, M., Stephens, G. J., Bouhours, M., Schultheis, C., Zhen, M., et al. (2008). Optogenetic Analysis of Synaptic Function. Nature methods, 5(10), 895-902.
Mukamel, R., Gelbard, H., Arieli, A., Hasson, U., Fried, I., & Malach, R. (2005). Coupling between Neuronal Firing, Field Potentials, and Fmri in Human Auditory Cortex. Science, 309(5736), 951-954.
Nir, Y., Dinstein, L, Malach, R., & Heeger, D. J. (2008). BOLD and Spiking Activity. Nature neuroscience, 11(5), 523-524.
Nir, Y., Hasson, U., Levy, L, Yeshurun, Y., & Malach, R. (2006). Widespread Functional Connectivity and fMRI Fluctuations in Human Visual Cortex in the Absence of Visual Stimulation. Neuroimage, 30(4), 1313-1324.
Ochsner, M., Dusseiller, M. R., Grandin, H. M., Luna-Morris, S., Textor, M., Vogel, V., et al. (2007). Micro-Well Arrays for 3d Shape Control and High Resolution Analysis of Single Cells. Lab on a Chip, 7(8), 1074-1077.
Owen, S., Green, A., Nandi, D., Bittar, R., Wang, S., & Aziz, T. Z. (2007). Deep Brain Stimulation for Neuropathic Pain. Acta Neurochirurgica-Supplementum Then Supplement-Wien-, 97(2), 111.
Perlovsky, L. (2009). "Vague-to-Crisp" Neural Mechanism of Perception. Neural Networks, IEEE Transactions on, 20(8), 1363-1367.
Prevedel, R., Yoon, Y.-G., Hoffmann, M., Pak, N., Wetzstein, G., Kato, S., et al. (2014). Simultaneous Whole-Animal 3d Imaging of Neuronal Activity Using Light-Field Microscopy. Nature methods, 11(7), 727-730.
Psota, J., Eastep, J., Miller, J., Konstantakopoulos, T., Watts, M., Beals, M., et al. (2007). ATAC: On-Chip Optical Networks for Multicore Processors. Massachusetts Institute of Technology.
Rajput, D., Crowder, S. W., Hofmeister, L., Costa, L., Sung, H.-J., & Hofmeister, W. (2013). Cell Interaction Study Method Using Novel 3d Silica Nanoneedle Gradient Arrays. Colloids and Surfaces B: Biointerfaces, 102,111-116.
Rutten, W. L., Smit, J. P., Frieswijk, T. A., Bielen, J. A., Brouwer, A. L., Buitenweg, J. R., et al. (1999). Neuro-Electronic Interfacing with Multielectrode Arrays. Engineering in Medicine and Biology Magazine, IEEE, 18(3), 47-55.
Sakaguchi, M., Kim, K., Yu, L. M. Y., Hashikawa, Y., Sekine, Y., Okumura, Y., et al. (2015). Inhibiting the Activity of CA1 Hippocampal Neurons Prevents the Recall of Contextual Fear Memory in Inducible ArchT Transgenic Mice. PloS one, 10(6), e0130163.
Scepanovic, M., Castillo, J. E., Barton, J. K., Mathine, D., Kostuk, R. K., & Sato, A. (2004). Design and Processing of High-Density Single-Mode Fiber Arrays for Imaging and Parallel Interferometer Applications. Applied optics, 43(21), 4150-4156.
Sotnikov, V., Perlovsky, L., & Deming, R. (2012). Implementation of Dynamic Logic Algorithm for Detection of EM Fields Scattered by Langmuir Soliton: INTECH Open Access Publisher.
Stoy, W., Yang, B., Capocasale, T., Whitmire, C., Liew, Y., Stanley, G., et al. ((2016)). High Yield Subcortical Patch Clamping in Vivo. Biophysical Journal, 110(3), 149a.
Sun, J., Timurdogan, E., Yaacobi, A., Hosseini, E. S., & Watts, M. R. (2013). Large-Scale Nanophotonic Phased Array. Nature, 493(7431), 195-199.
Timurdogan, Erman, Cheryl M. Sorace-Agaskar, Jie Sun, Ehsan Shah Hosseini, Aleksandr Biberman, and Michael R. Watts. "An ultralow power athermal silicon modulator." Nature communications 5 (2014).
Tsunematsu, T., Kilduff, T. S., Boyden, E. S., Takahashi, S., Tominaga, M., & Yamanaka, A. (2011). Acute Optogenetic Silencing of Orexin/ Hypocretin Neurons Induces Slow-Wave Sleep in Mice. The Journal of Neuroscience, 31(29), 10529-10539.
Tufail, Y., Matyushov, A., Baldwin, N., Tauchmann, M. L., Georges, J., Yoshihiro, A., et al. (2010). Transcranial Pulsed Ultrasound Stimulates Intact Brain Circuits. Neuron, 66(5), 681-694.
Wang, H., Peca, J., Matsuzaki, M., Matsuzaki, K., Noguchi, J., Qiu, L., et al. (2007). High-Speed Mapping of Synaptic Connectivity Using Photostimulation in Channelrhodopsin-2 Transgenic Mice. Proceedings of the National Academy of Sciences, 104(19), 8143-8148.
Watts, M. R., Trotter, D. C., Young, R. W., & Lentine, A. L. (2008). Ultralow Power Silicon Microdisk Modulators and Switches. Paper presented at the 5th Annual Conference on Group IV Photonics.
Wentz, C. T., Bernstein, J. G., Monahan, P., Guerra, A., Rodriguez, A., & Boyden, E. S. (2011). A Wirelessly Powered and Controlled Device for Optical Neural Control of Freely-Behaving Animals. Journal of neural engineering, 8(4), 046021.
Zhang, F., Wang, L.-P., Boyden, E. S., & Deisseroth, K. (2006). Channelrhodopsin-2 and Optical Control of Excitable Cells. Nature methods, 3(10), 785-792.
Zhang, F., Wang, L.-P., Brauner, M., Liewald, J. F., Kay, K., Watzke, N., et al. (2007). Multimodal Fast Optical Interrogation of Neural Circuitry. Nature, 446(7136), 633-639.
Zhao, Y., Hu, C., Song, L., Wang, L., Shi, G., Dai, L., et al. (2014). Functional Graphene Nanomesh Foam. Energy & Environmental Science, 7(6), 1913-1918.
Zortman, W. A., Trotter, D. C., & Watts, M. R. (2010). Silicon Photonics Manufacturing. Optics express, 18(23), 23598-23607.
Zorzos, A. N., Boyden, E. S., & Fonstad, C. G. (2010). Multiwaveguide Implantable Probe for Light Delivery to Sets of Distributed Brain Targets. Optics letters, 35(24), 4133-4135.
Emery N Brown, Robert E Kass, and Partha P Mitra Multiple neural spike train data analysis: state-of-the-art and future challenges. Nature neuroscience, 7(5):456-461, 2004.
Gyorgy Buzsaki, Costas A Anastassiou, and Christof Koch. The origin of extracellular fields and currents eeg, ecog, lfp and spikes. Nature reviews neuroscience, 13(6):407-420, 2012.
Michael S Lewicki. A review of methods for spike sorting: the detection and classification of neural action potentials Network: Computation in Neural Systems, 9(4):R53-R78, 1998.
Jonathan W Pillow, Jonathon Shlens, EJ Chichilnisky, and Eero P Simoncelli. A model-based spike sorting algorithm for removing correlation artifacts in multi-neuron recordings. PloS one, 8(5):e62123, 2013.
Hernan Gonzalo Rey, Carlos Pedreira, and Rodrigo Quian Quiroga. Past, present and future of spike sorting techniques. Brain research bulletin, 119:106-117,2015.
Jiri Wild, Zoltan Prekopcsak, Tomas Sieger, Daniel Novak, and Robert Jech. Performance comparison of extracellular spike sorting algorithms for single- channel recordings Journal of neuroscience methods, 203(2):369-376, 2012.

* cited by examiner

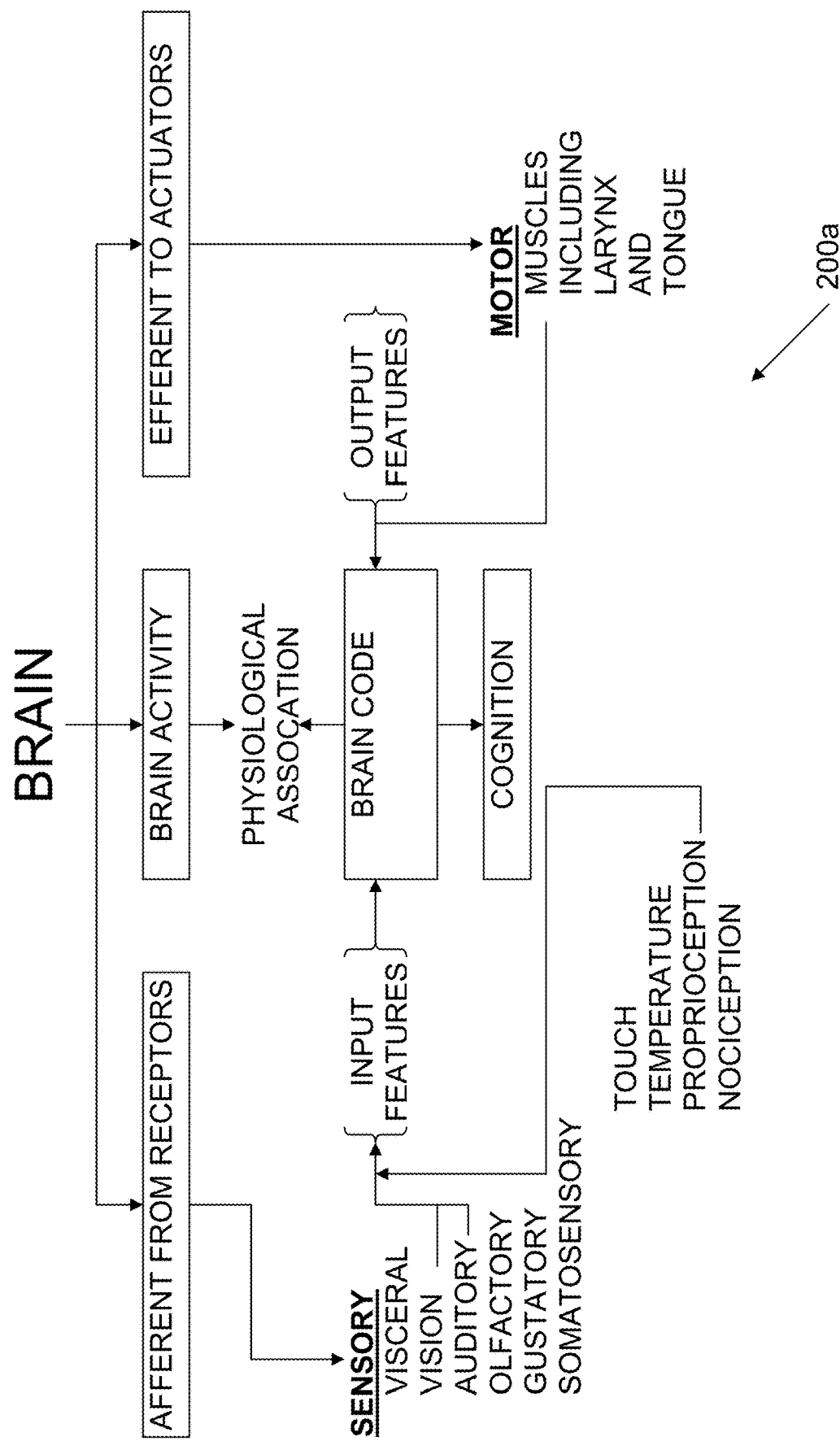

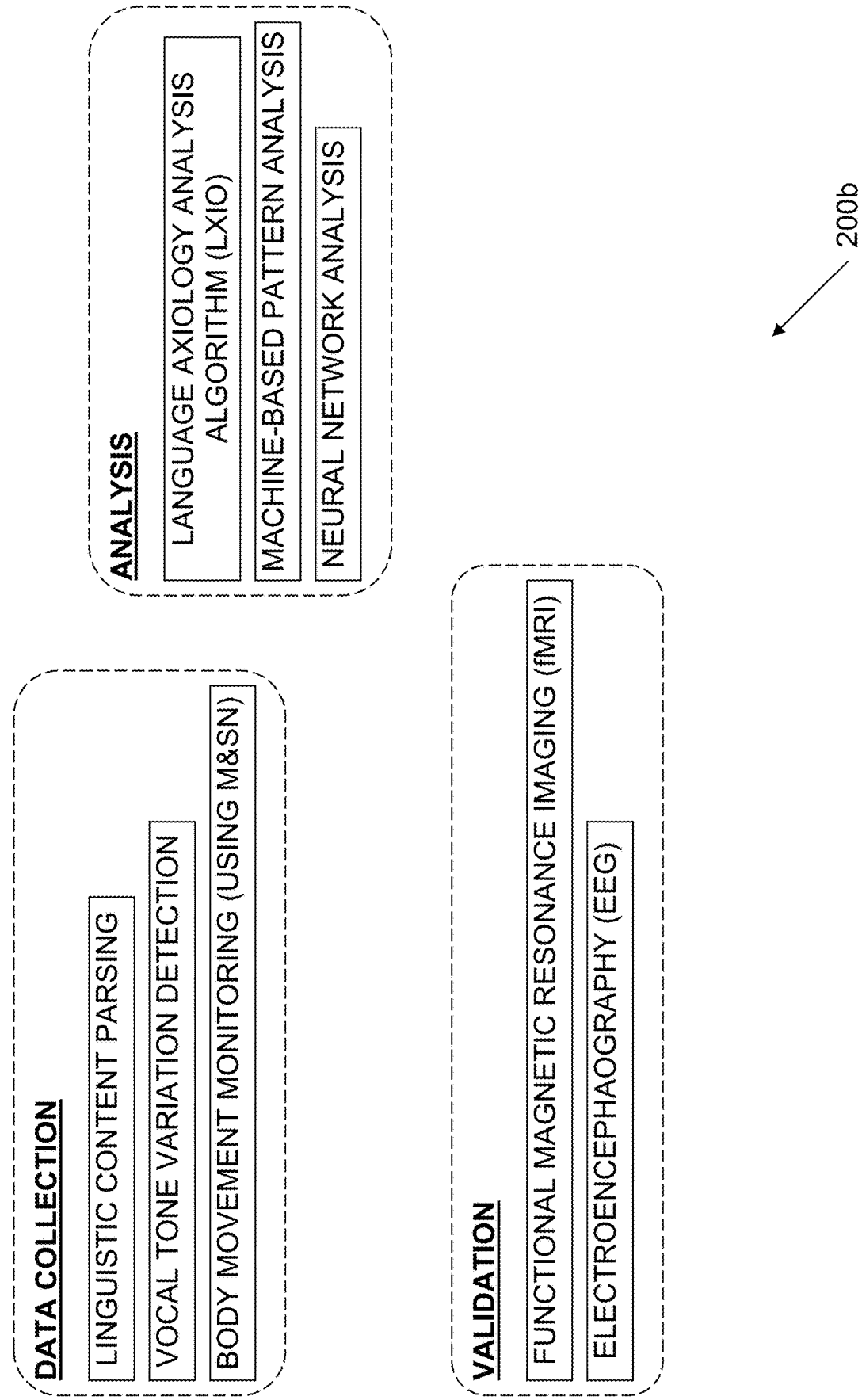

NEUROANALYTIC, NEURODIAGNOSTIC, AND THERAPEUTIC TOOLS

CROSS-REFERENCE TO RELATED APPLICATIONS

This application claims the benefit of U.S. Provisional Application No. 62/308,212, filed Mar. 14, 2016, the contents of which are incorporated herein in their entirety.

BACKGROUND

The present invention relates to multimodal diagnostic systems and methods for detecting neurological disorders, such as Alzheimer's disease (AD), Parkinson's disease (PD), depression, PTSD, schizophrenia, dementia, and many others.

Research in this area has been ongoing, for example, having begun in the 1990s with a PhD study of intentionality within the respective contexts of human thought, communication, and command structures. This initial work was seminal and resulted in the redesign of command and control systems throughout the U.S. Military, where it was used to develop systems for predictive conflict resolution and the enhancement of the human-driven activities of writing and issuing orders across all echelons, enabling automated cross-check capabilities. Intention Awareness (IA) was applied to develop COSMOS (Coalition Secure Management and Operations System) of the Defense Information Systems Agency (DISA) to enable unambiguous protected sharing of command and control (C2) information among international coalition partners. IA was also used to develop a predictive, neurologically-inspired wireless communications network architecture that radically increased the range, throughput, and security of military communications in the field.

IA has been applied within the U.S. Military to understanding Post Traumatic Stress Disorder (PTSD) and Traumatic Brain Injury (TBI) and to develop tools to aid in the diagnosis and treatment of these disorders. A proposed addition to the C3I had called for embedding IA sensors within combat helmets to monitor neurophysiological states for warfighter stress levels and degrees of command confidence. Within a linguistic domain, IA has been used for lexical analysis to determine the manifestations of the internal mind states of the perpetrators of violent events and the patterns of online dissemination of radical materials. These IA systems were applied to the Radicalization Watch Project (RWP) to find, identify and authenticate materials generated by terrorist groups and analyze discourse to determine reasoning patterns, perceptions, and intentions to help drive psychological operations. This work with linguistic processing later developed into a more formal study of predictive linguistics, an area of research at the intersection of formal linguistics, cognitive computing, and mathematics.

These works were further developed at MIT over the course of several years evolving into the Mind Machine Project and later the MIT Synthetic Intelligence Lab, where research focused on producing not only Artificial Intelligence, but Artificial Consciousness (AC). Nanotechnology was explored as a method of computer-brain interfacing for several years and it was eventually determined that an intimate understanding of neurological processes was required to effectively replicate these processes within computer architectures (software and hardware). As a result, IA and AC were brought to Oxford to research the human brain.

Further research focused on discovering the most fundamental unit of human thought (the layer upon which all other layers are constructed), existing at the smallest scale of neurophysiological operation. In 2014, this fundamental layer was discovered to be a photonic signaling system endogenous within the cerebral cortex, powered by mitochondrial free radical production and mediated by neuropsin (OPN5), a bistable photopigment. The bistable nature of this circuit and its associated (5:3) photoelectric exchange strongly suggest that there exists a unary/quantum basis to cognition.

Progress in understanding the global organization of brain function has remained elusive due in large part to the multiscale nature of brain activity. Normal operation of the brain is characterized by complex dynamics at multiple levels, ranging from the microscopic scale of single neurons to the mesoscopic level of cortical columns and finally to the macroscopic level of the whole brain. The brain is an intrinsically multiscale, multilevel organ operating across spatial scales range from nanometers (proteins) to meters (the human body) and temporal scales from picoseconds (atomic interactions) to years (the lifespan of a human being).

Accordingly, a need arises for a multimodal approach to understand the operation of this multiscale organ and model its behavior successfully, from microscale to macro.

SUMMARY

Embodiments of the present invention may provide multimodal diagnostic systems and methods for detecting neurological disorders, such as Alzheimer's disease (AD), Parkinson's disease (PD), depression, PTSD, schizophrenia, dementia, and many others. Such techniques may synchronously capture data across each of the brain organizational layers and reliably interpret it.

For example, in an embodiment, a system for monitoring brain activity may comprise a plurality of sensors, each adapted to monitor a physical or physiological parameter and output a signal representing the monitored physical or physiological parameter, wherein the plurality of sensors includes at least one sensor configured to monitor a brain activity parameter, a data collection device adapted to receive the plurality of signals from the plurality of sensors and to process the signals to form digital data representing the monitored physical or physiological parameters, and a data processing device adapted to process digital data representing the monitored physical or physiological parameters to determine presence of a neurological disorder or condition.

In an embodiment, the sensors may comprise at least a plurality of sensors selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors. At least some of the sensors may be adapted in an earbud device and the earbud device may comprise at least one component selected from a group comprising: digital storage, a controller, a pulse oximetry sensor, an TAP sensor, a digital signal processor, a kinetic power source, EEG sensors, ECG sensors, a balanced armature transducer, a microphone, a gyroscope, an accelerometer, a magnetometer, a wireless transceiver, and an optical touch sensor. The at least one sensor configured to monitor a brain activity parameter comprises a carbon nanotube sensor in contact with neural tissue.

In an embodiment, a computer-implemented method for monitoring brain activity may comprise receiving from each of a plurality of sensors, a signal representing a monitored physical or physiological parameter, wherein the plurality of sensors includes at least one sensor configured to monitor a brain activity parameter, processing the received signals to form digital data representing the monitored physical or physiological parameters, and processing digital data representing the monitored physical or physiological parameters to determine presence of a neurological disorder or condition.

In an embodiment, a system for monitoring brain activity may comprise a processor, memory accessible by the processor, and computer program instructions stored in the memory and executable by the processor to perform receiving from each of a plurality of sensors, a signal representing a monitored physical or physiological parameter, wherein the plurality of sensors includes at least one sensor configured to monitor a brain activity parameter, processing the received signals to form digital data representing the monitored physical or physiological parameters, and processing digital data representing the monitored physical or physiological parameters to determine presence of a neurological disorder or condition.

BRIEF DESCRIPTION OF THE DRAWINGS

The details of the present invention, both as to its structure and operation, can best be understood by referring to the accompanying drawings, in which like reference numbers and designations refer to like elements.

FIG. 2a is an exemplary diagram of functions that may be performed by the Biological Co-Processor System shown in FIG. 1.

FIG. 2b is an exemplary diagram of functions that may be performed by the Biological Co-Processor System shown in FIG. 1.

DETAILED DESCRIPTION

Embodiments of the present invention may provide multimodal diagnostic systems and methods for detecting neurological disorders, such as Alzheimer's disease (AD), Parkinson's disease (PD), depression, PTSD, schizophrenia, dementia, and many others. Such techniques may synchronously capture data across each of the brain organizational layers and reliably interpret it.

Embodiments of the present systems and methods may be based on the Fundamental Code Unit (FCU), Brain Code (BC), and Intention Awareness (IA) theorems—the FCU provides the underlying mathematical framework to support multimodal data analysis and learning, BC algorithms are used to identify key patterns and IA is used to meaningfully relate these patterns. These theorems provide the capability to treat the entire brain system as a self-similar linguistic engine, with each physiological process a simple expression of intent. These expressions may cascade upward through successive layers of organization to eventually manifest as higher-order behavior: thought, movement, speech, etc. This coherence is what enables language and movement to reveal so much information about a patient's neurological state, even when the patient is not discussing their condition or performing any particular test. The mathematical framework behind the FCU remains consistent in mapping this system from the lowest levels (sub-neural) to the highest orders of expression (behavioral and linguistic).

There are many companies building sensors, AI-powered healthcare services and even brain implants, but embodiments of the present systems and methods may provide the capability to map neurobehavioral data, neurological processes, and all other forms of patient data across a common mathematical framework. The FCU is the key to integrating all of these various layers and data types to find Brain Codes and confers a sustainable competitive advantage over any other company attempting a similar method of analysis. The process of mapping Brain Codes is the process of decoding the Language of the Brain.

In performing multimodal diagnostics, a battery of methodologies may be utilized to analyze each data type in different ways. For example, audio may be examined for tonality, pitch, projection, response delay, volume, frequency, vocal tremor and more even before it is broken down into text and analyzed for cognitive response, emotional state, sentiment analysis and other factors.

Figure 1:
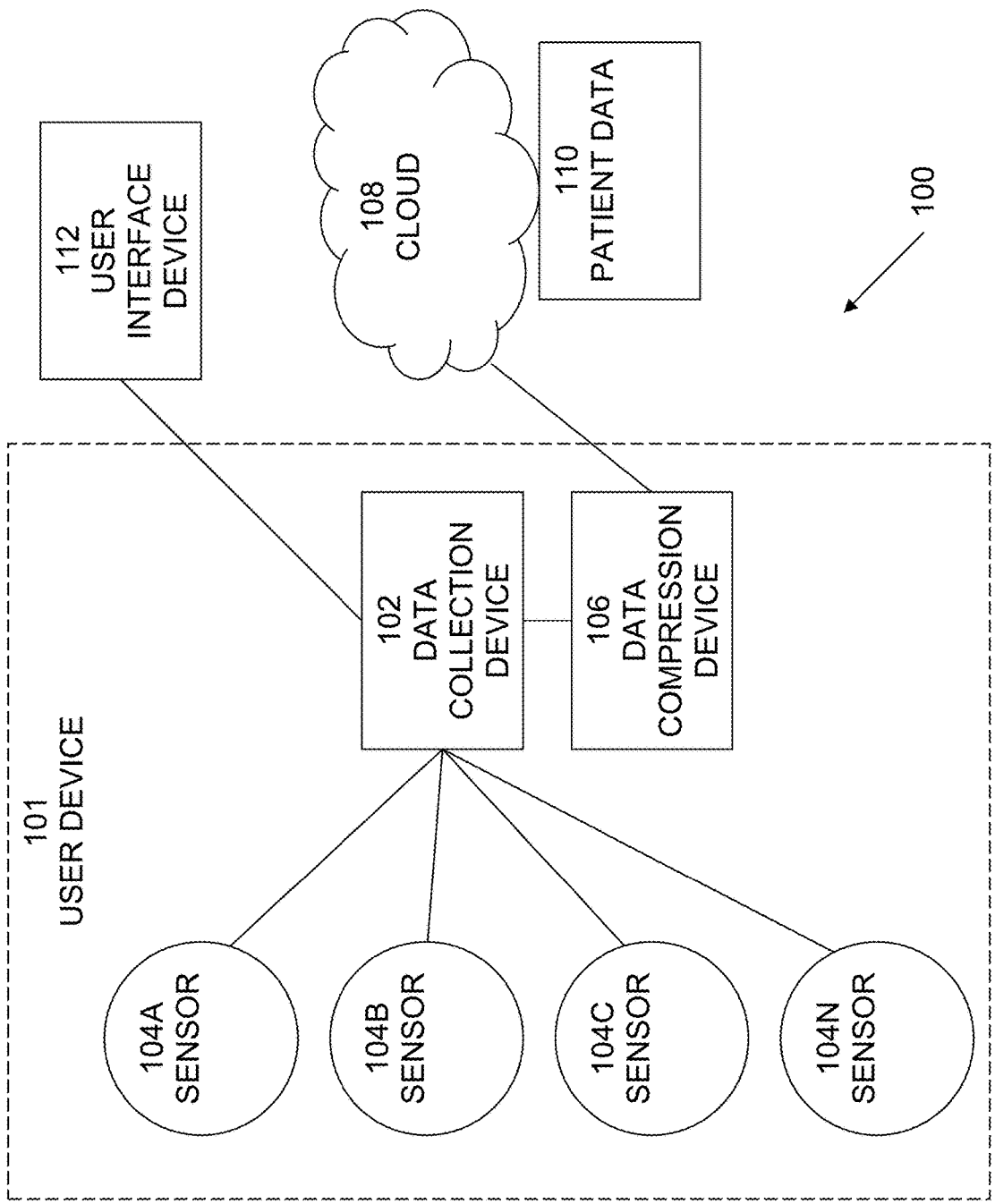
FIG. 1 is an exemplary diagram of an embodiment of a Biological Co-Processor System (BCP).

An exemplary embodiment of a Biological Co-Processor System (BCP) 100 is shown in FIG. 1. The BCP 100 may be a neurodiagnostic system that may reliably detect many diseases formerly considered undiagnosable, such as Alzheimer's, Parkinson's and dementia. In addition to working with neurodegenerative disorders, prototypes of BCP 100 may be used to help diagnose, track, and manage PTSD in active and veteran troops. BCP 100 may also be used to construct systems for suicide prevention and the early detection of depression.

In embodiments, BCP 100 may include user device 101, which may include a mass data collection device 102, using a variety of sensors, such as sensors 104A-N to synchronously capture audio, video, EEG, ECG, heart rate, breathing rate, blood pressure, body temperature, head movement, body posture, blood oxygenation levels and more. The BCP data compression device 106 may then assemble this data into a compressed stream to send it to the cloud 108 for storage and evaluation. This technique is both extensive and extensible—whenever a new biomarker is found involving any of these factors, BCP 100 can simply add that test to the existing process.

Once a patient profile has been created in the cloud, any and all types of patient information 110 may be uploaded to the system—genetics, prescriptions, diet, height, weight, scan data (MRI, PET, CT, MEG, etc.), clinician or therapist notes, patient writings (social media, chat, email), environmental/work factors, family history, psychological history, browser history, phone usage history—all of these data types and more may be added to enable the most comprehensive analysis possible.

In embodiments, BCP 100 may perform functions 200a and 200b, as shown in FIGS. 2a and 2b.

In embodiments, BCP 100 may be built upon a deep machine learning architecture, and be designed to improve with each use, as it collects an ever-increasing amount of patient data to analyze, steadily growing a database of key health and disease biomarkers. In addition to compiling patient data, the Company will also be actively aggregating as much commercial, open source, public and private research as possible for its Artificial Intelligences (AIs) to learn from, including disease-specific databases such as Unified Parkinson's Disease Rating Scale (UPDRS), Parkinson's Progression Markers Initiative (PPMI) and others.

BCP 100 may enable doctors to capture far more patient data than ever before and may provide clinicians with clear, quantitative measurements, trends and guidance that they can use to not only help diagnose a disease but also objectively track its progression (and the efficacy of various treatments) over time. BCP 100 is also highly convenient, saving the physician from needing to manually conduct a number of vital tests. BCP 100 may include an in-earbud infrared sensor, for example, is able to take a highly accurate body temperature reading in only two seconds, which it promptly sends to an app on the a user interface device 112, such as a clinician's tablet or smartphone. In the case of prescribed home use, patients will be able to transparently share these vitals with their doctor. In the case of the consumer, users will be able to choose whether or not to share their vitals with a physician (and which physician). In collecting all of this patient data to the cloud, BCP 100 may solve many of the record portability issues encountered when patients move from physician to physician, silo to silo.

The portable nature of user device 101 may make the device quite useful in the field, as well. Ambulatory and first responder medics will be able to use the system to more thoroughly determine the nature and extent of trauma or injury at a crisis location. Similarly, smaller clinics, such as those located at Universities, within companies and in schools, will have sufficient space for such a system, and presently have no means of even determining the extent of a concussion, let alone detecting neurological disorders or common, treatable conditions such as depression or ADHD.

In embodiments, BCP 100 may be entirely self-service, which is advantageous for companies and universities seeking a low-cost means of providing healthcare screening for high volumes of people.

In embodiments, user device 101 may be comfortably wearable and may be routinely sent home with patients to collect neurobehavioral data between visits. Neurological and psychological symptoms don't always manifest while the patient is at the clinic; these are often triggered by external factors not present, such as stressful relationships, fitful sleeping patterns, pharmaceutical influence, hormonal patterns, the strain of exercise, diet, etc. Patients wearing user device 101 while experiencing an episode or seizure will be able to provide far more useful data than dozens of visits under non-triggered conditions ever would. Remote monitoring also enables doctors to observe their patients for hours, weeks, or even months at a time, potentially reducing the need for in-person clinic visitations (and long-term stays).

The extended-wear capability of user device 101 may also make the device of particular interest to companies testing immediate and long-term neurophysiological reaction to a particular stimulus (such as pharmaceutical companies). BCP 100 may be used for quantitatively testing the effects of new drugs and for testing the effects of a new drug upon a particular individual. Drugs have interactions and affect different people differently and so the safest possible means of adding or changing one's prescription would be to send them home with a device to monitor their physiology for a few days and ensure that the drug is working, with no unintended effects.

Figure 3:
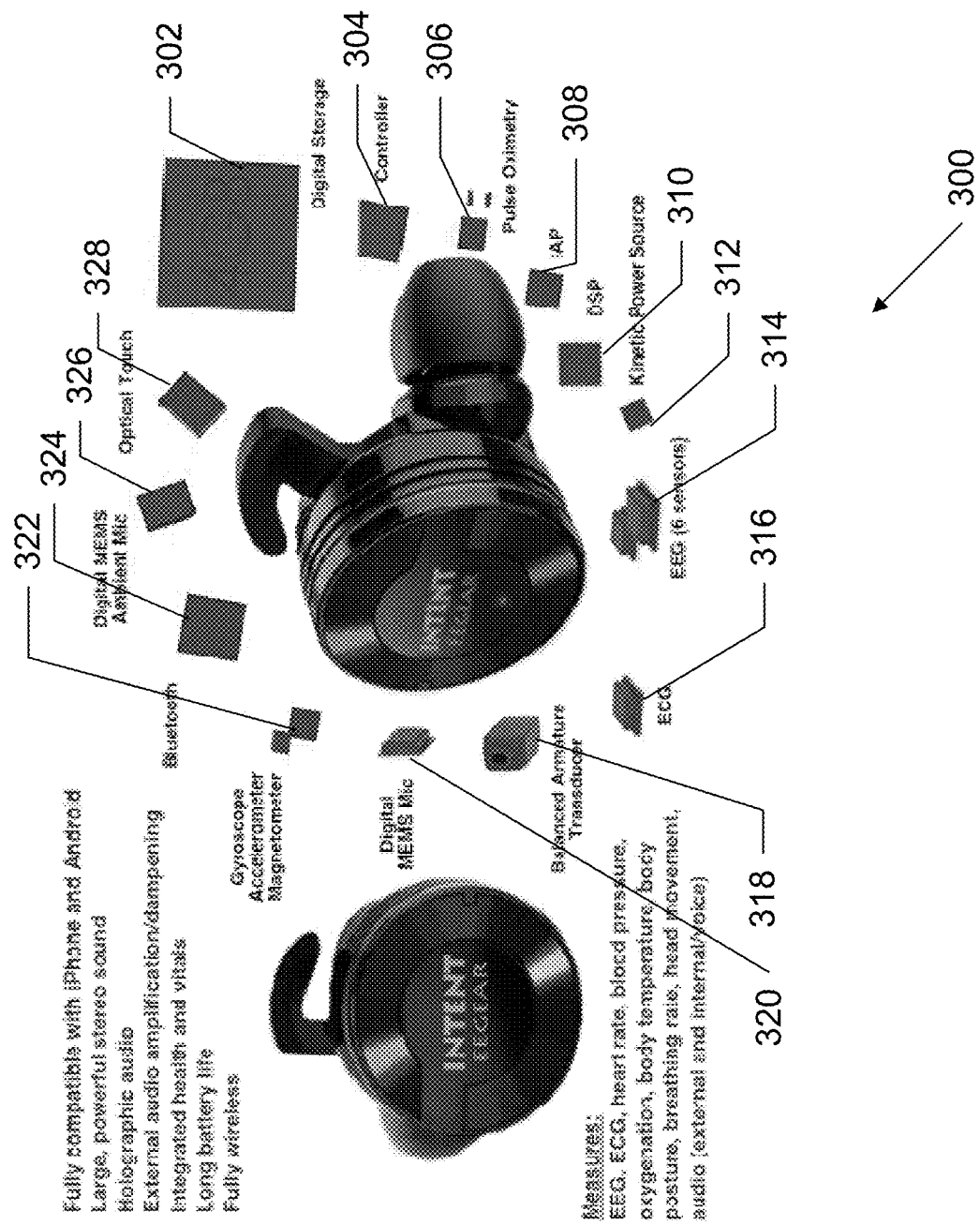
FIG. 3 is an exemplary diagram of sensor-equipped earbuds that may be utilized by the Biological Co-Processor System shown in FIG. 1.

An exemplary user device 101, in the form of sensor-equipped earbuds 300, is shown in FIG. 3. Such earbuds may include a number of features. For example, earbuds 300 may be compatible with user interface devices 112, such as iOS and Android smartphones, tablets, personal computers, etc. Earbuds 300 may provide user features such as stereo sound, holographic audio, external audio amplification/dampening, long battery life, and may be fully wireless. Earbuds 300 may provide health features such as integrated health and vitals, physical parameter measurements, such as EEG, ECG, heart rate, blood pressure, blood oxygenation, body temperature, body posture, breathing rate, head movement, etc. Earbuds 300 may include components such as digital storage 302, controller 304, pulse oximetry sensor 306, IAP sensor 308, digital signal processor 310, kinetic power source 312, EEG sensors 314, ECG sensors 316, balanced armature transducer 318, digital Microelectromechanical systems (MEMS) microphone 320, gyroscope, accelerometer, and/or magnetometer 322, Bluetooth transceiver 324, digital MEMS ambient microphone 326, and optical touch sensor 328. In this age of mobile computing, quality earbuds are in high demand, with the highest-end models selling for thousands of dollars while offering little or no additional functionality beyond slight improvements in sound quality. The cost of these devices have come down considerably in the past few years and so there is an opportunity to deliver its health monitoring and emotional detection capabilities to the masses with a consumer version of a clinical BCCS earbud.

Consumer wearables, such as activity monitors, bands and smartwatches, all provide users with varying degrees of health information. Most measure daily activity (steps), heart rate and sleep quality. Some track the user's running statistics, eating habits and a few exercises. However, the ear is believed to be the single best place on the body to collect this data.

Wristbands have difficulty even reading heart rate with reliable accuracy, due to variance in skin types and tones, noise from arm movements and other factors. Optical heart rate monitoring methods and even ballistocardiograms struggle for accuracy in such a noisy environment. The wrist is probably one of the worst and noisiest places to put a body sensor. For this reason alone, the BCCS earbud should be able to provide more biometric information, more accurately, than any wristband or watch.

The ear is also one of the best locations for collecting neurological information, such as EEG. Neurological data provides the health-conscious user with yet another layer of information—useful to some, but not many. The real value to adding EEG to an earbud (beyond neurological health diagnostics and monitoring) is that it enables third-party developers to powerfully augment their applications with emotional sensitivity and (a basic degree of) neuro-prosthetic control. This EEG feed may be processed by decoding it into several actionable triggers that developers may use in their applications. This capability may be particularly useful to videogame developers, as much of the gameplay and environment they develop is nondeterministic/procedural in nature and designed to change in response to user interaction. With the BCCS, games may be able to respond to both conscious and unconscious reactions.

A discreetly wearable EEG may enable VR developers to add entirely new levels of interactivity and intelligence to their experiences. Games may be able to sense if the user is engaged, excited, scared, or bored, and pivot gameplay accordingly. Developers may be able to gently pulse the virtual environment along with the user's heartbeat or breathing rate, or affect the music volume, tempo of pace of gameplay. Similarly, developers of educational software may be able to sense how involved and interested (or confused/frustrated) the student is, allowing the content to pivot itself to consider it from a different angle and keep them engaged (or notify the teacher). A Software Development Kit (SDK) for the BCCS may enable developers to add these new levels of interactivity to their mobile apps, games, or VR worlds. In an embodiment, BCCS products may come equipped with the same neurodiagnostic capabilities as clinical devices, so widespread consumer release of the technology may enable many now suffering from undiagnosed neurological conditions to find the support they need. For those diagnosed, the device may provide assistance with ongoing management, mapping treatment efficacies and disease progression (personal and aggregate). The Clinical and Consumer BCCS devices may be quite similar; the Clinical model may simply have a higher sensitivity, quality and price and so may only be available upon successful FDA certification and medical device coding.

Pharmaceutical companies may seek to make use of the Clinical BCCS to capture high quality neurophysiological data over time, the Consumer BCCS may be useful for anyone conducting polls, market research, or clinical studies. The utility of EEG in many of these environments has been verified positive but the cost, bulky wires and difficulty of operating traditional EEG systems has kept them from being used widely in standard polls, taste tests, or market research surveys. Neurophysiological data is often more honest and reliable than the verbal or written opinions provided by the test participant, so a very small and simple EEG would be tremendously helpful to each of these groups. Therapists and counselors may likewise benefit from a Consumer BCCS, even without a medical coding, as it would provide them with an additional window of insight into what their patient is thinking and feeling, during their session In an embodiment, a component of the BCCS system is its linguistic processing capabilities, which are powered by text, audio, and video. Such content is widespread and may lead to the development of a number of general and disease-specific apps and websites over the coming years. For example, a website may help promote awareness of NOs and NODs while teaching users how to both self-diagnose and manage their conditions. Specific environments requiring immediate analysis of incoming audio, such as corporate call centers, crisis numbers and suicide hotlines may all benefit from the features of this one component of the BCCS system. Specific environments requiring immediate analysis of text, such as sentiment analysis across social media, emails, call center logs or other corpus may also be handled by components of the BCCS system. The entire BCCS system may be designed to be modular for the express purpose of making use of some or all of its methods of analysis. These services may be powered by the same cloud FCU that powers the clinical system.

Once a significant volume of BCCS devices are in use, a tremendous amount of user data may be collected. Within a health context, this data may be mined to find biomarkers and functional Brain Codes. Within a consumer context, however, this data may be mined for a range of commercial purposes. Just as the BCCS may provide real-time user insight to the therapist, usage data may also provide a tremendous amount of analytical value to marketers.

The BCCS and FCU are designed to aggregate and meaningfully combine data of all kinds and types. When applied to a consumer context, this may include mapping BCCS data to media consumption, enabling the matching of users with content they are apt to like, based on other users with similar signatures, personal past history and present mood. Just as analytics companies, such as Google, map search terms to web pages viewed, embodiments may map neurological states (and vitals) to all media experienced. This may allow tracking of how levels of engagement vary over the course of watching a movie, for example. Likewise, the system may gauge engagement for commercials.

Mobile, real-time neurological data is entirely new and so numerous applications for the data may arise. Mapping neurological states to location, for example, may allow customers to map their pleasure or displeasure without having to explicitly post a review. The aggregate of this data may be able to show a happiness heat map, at present or over time, providing feedback that could potentially draw customers to desirable events. Some apps may be built using this neuroanalytic data, but the largest use may come from third-party applications written to make specific use of the, via an Application Programming Interface (API).

In an embodiment, each time that product is experienced by a BCCS user over the course of their daily life, the corresponding EEG may be associated with it. This data, once aggregated across a sample of any significant size, may provide a great deal of insight into customer perception and behavior. Finding disease biomarkers within a sea of biometric data is far more difficult than matching people to products, so there may eventually prove to be more value in the usage data our customers leave behind than in the sale of the devices themselves.

Embodiments may provide security and anonymity to the data, so that neuroanalytics may provide marketers with powerful tools. Television allowed marketers to know how many times a particular commercial aired within a given market. The web allowed marketers to see how many times their ad was viewed (and clicked). Embodiments of the present system and methods may allow marketers to finally see how their ad (or product) is actually experienced by their target customer. Real-time neuroanalytics may also be used to inform dynamic mobile advertising platforms, so advertisers can avoid running ads to annoyed users (or maybe push an ad, if the annoyed user in standing inside a competitor's store). Advertisers could buy best time of mood, just as best time of day (or day of the week) can be sold, presently. In a world of widespread EEG adoption, daily user interaction with products, people, and places automatically informs collective opinion.

Deep Brain Stimulation (DBS) is a neurosurgical procedure involving the implantation of a neurostimulator which sends electrical impulses, through implanted electrodes, to specific parts of the brain for the treatment of movement and affective disorders. DBS in select brain regions has provided therapeutic benefits for otherwise-treatment-resistant movement and affective disorders such as Parkinson's disease, essential tremor, dystonia, chronic pain, major depression and obsessive-compulsive disorder (OCD). The Food and Drug Administration (FDA) approved DBS as a treatment for essential tremor in 1997, for Parkinson's disease in 2002, dystonia in 2003, and OCD in 2009. DBS is also used in research studies to treat chronic pain and PTSD and has been used to treat various affective disorders, including major depression. DBS has been used to successfully treat about 100,000 patients worldwide with movement disorders such as Parkinson's disease.

Conventional DBS systems use electricity to shock neurons and so are only capable of disrupting circuitry within a region. Optogenetic systems may provide for both temporal resolution and cell-type specificity, as they are able to selectively excite and silence individual neurons (or specific groups of neurons). Optogenetic technologies may provide the means for simultaneously activating and recording neural potentials, enabling true circuit analysis and finally allowing researchers to interactively map brain circuits. The technology may also enable functional neurosurgery at a far smaller scale than electrical DBS allows, since optogenetic systems may selectively control neuronal groups. Embodiments of the present systems and methods may utilize optogenetic systems and may include an autonomous brain implant, as described below.

Figure 4:
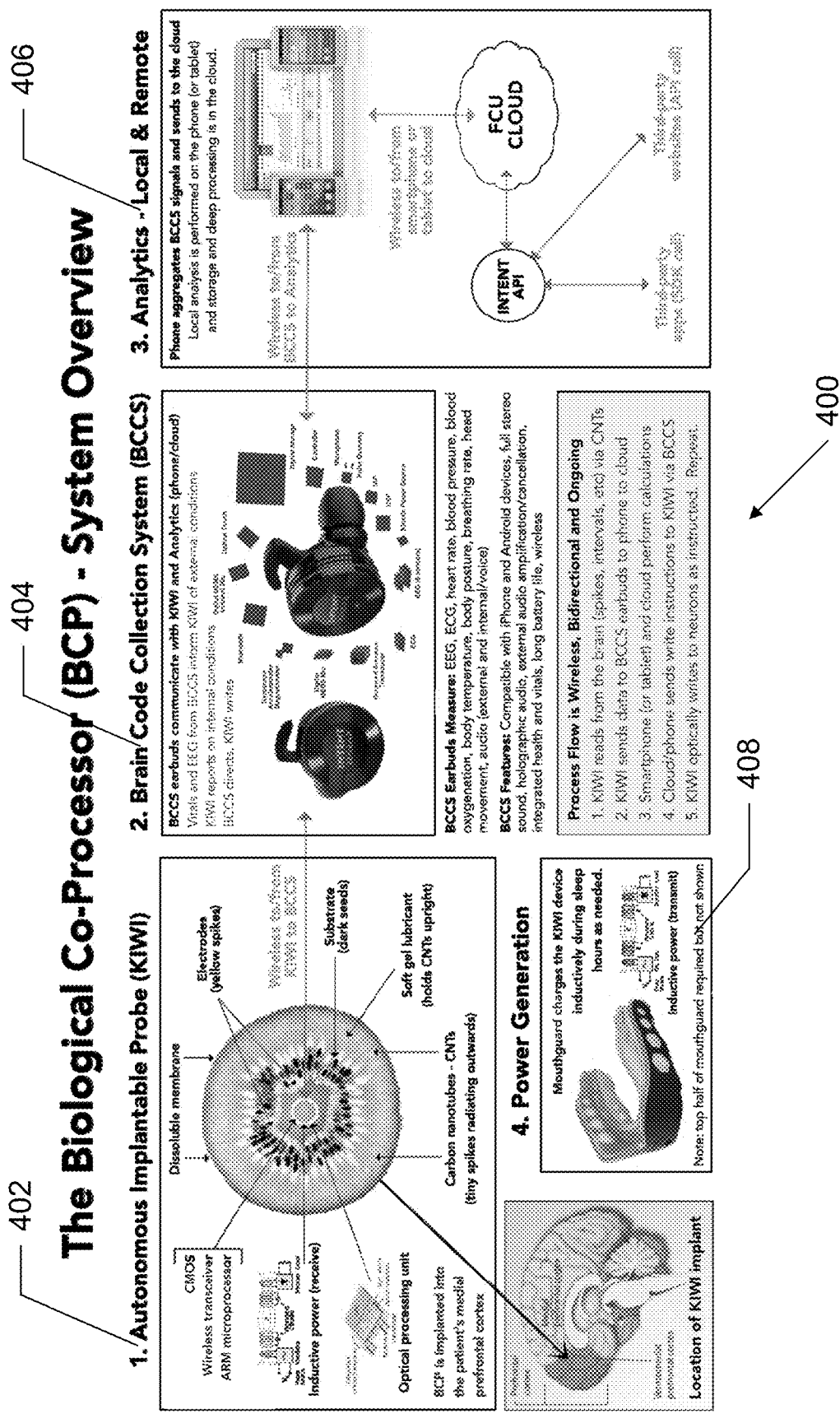
FIG. 4 is an exemplary diagram of an embodiment of a Biological Co-Processor System (BCP).

Embodiments of the present systems and methods may include the Biological Co-Processor (BCP) system 400, an example of which is shown in FIG. 4. BCP 400 may include four main components—an autonomous implantable probe 402, a Brain Code Collection System 404, local and/or remote analytics engine 406, and power source 408.

BCP 400 may include an optical neural implant powered by a microscale FCU kernel that is capable of intelligently reading and writing to neural circuitry in real-time. First-generation BCP devices may be microscale and capable of interactively monitoring and regulating local circuits within boundary conditions. In embodiments, these devices may be designed with Analog Logic Automata (ALA) and RALA chip architectures (first developed at the Mind Machine Project and later evolved at the MIT Synthetic Intelligence Lab), to natively process (and compress) these neural signals.

BCP 400 may include a microfabricated carbon nanotube (CNT) neural interface (autonomous implantable probe 402), a processor unit for radio transmission and communicating input and output (I/O), a light modulation and detection silicon photonic chip, and an independent receiver system where all the processing will preside. It may be self-regulating, and perform reading and writing near real-time. Transcranial Pulse Ultrasound (TPU) may be used to adhere the CNT to the cells. Optogenetic neurostimulation may be autonomously guided by analytics powered by computational algorithms based on Fundamental Code Unit (FCU) architecture, which provides high rates of throughput and compression.

BCP system 400 may be unique in its extensive use of CNTs, with a deeply implanted CNT patch and subdural transceiver that allows reading of neurons at the surface and in 3D. CNT fibers may allow bidirectional input and output whereas optical fibers can only transmit one way into the brain. The microchip that may be attached to the CNT patch may be a neurologically inspired architecture (RALA), which will enable high-speed, native (unary) processing and parallel streaming of neural recording. BCP 400 may autosense neuron activity and guide the nanotube for light stimulation. This technique may allow precision targeting in near real time. The physical architecture of this neural probe may use a spiked 3D design (within a dissoluble membrane) to ensure maximum points of neural contact.

In embodiments, BCP 400 may be nanoscale, un-tethered and self-powered. These nanoscale devices may use an optical system present within the human neocortex. This circuit is mediated by neuropsin (OPNS), a bistable photopigment, and is driven by mitochondrial free radical production. Components of this circuit may be relatively simple proteins that may be cultured or engineered to produce chips from organic tissue. This bistable circuit may be a self-regulating cycle of photon-mediated events in the neocortex involving sequential interactions among three mitochondrial sources of endogenously-generated photons during periods of increased neural spiking activity: (a) near-UV photons (~380 nm), a free radical reaction byproduct; (b) blue photons (~470 nm) emitted by NAD(P)H upon absorption of near-UV photons; and (c) green photons (~530 nm) generated by NAD(P)H oxidases, upon NAD(P)H-generated blue photon absorption. The bistable nature of this nanoscale quantum process provides evidence for an on/off (UNARY +/−) coding system existing at the most fundamental level of brain operation and provides a solid neurophysiological basis for the FCU. This phenomenon also provides an explanation for how the brain is able to process so much information with slower circuits and so little energy—quantum tunneling. Computers built from such material would be orders of magnitude faster than anything developed to date. Neural implants built from such material would be both intelligent and self-powered. These devices would interface with the brain at a scale many orders of magnitude smaller than even optogenetics, which only scales down to the individual neuron.

Nearly all neurological examinations conducted today are relatively quick, bedside interviews that are highly subjective and almost entirely dependent upon doctor sensitivity. While an experienced neurologist will often know what to ask and look for in a patient, a general physician, nurse or caregiver may not. Since patients will usually only ever visit a neurologist if their doctor tells them to, most people suffering with these diseases are never diagnosed or treated for it. Only 5-10% of those suffering from neurological disorder ever even end up visiting a neurologist or psychiatrist.

With so few cases being diagnosed, more advanced neurological screening and awareness is certainly required, at all levels. Neurological disorders are not only invisible, they are also often tied to multiple comorbidities and so can be remarkably difficult to diagnose. Without the use of People with brain disorders Total Population multimodal methods, many significant neurological diseases, such as Alzheimer's Disease and Parkinson's Disease, can only be reliably diagnosed post-mortem.

Many patients suffering from neurological disorders may be diagnosed and treated by their primary care doctors, who lack the tools and training to tackle the complexities of either recognizing or treating brain disorders. For this reason, more than half of all brain conditions are misdiagnosed and mis-medicated. For those few patients who are properly diagnosed, their diagnosis often comes too late, as NODs begin to exhibit macro-level indicators (such as tremor) long after most of the internal damage has already been done. Early diagnosis is critical for being able to treat these diseases effectively.

Neurological Disorders (NDs) comprise over 600 known disorders and affect over 50 million people worldwide—collectively, these disorders constitute the single largest cost in healthcare today. NDs include physical conditions such as Traumatic Brain Injury (TBI) or epilepsy; psychological disorders such as depression or schizophrenia; and degenerative conditions such as Alzheimer's Disease (AD). Neurological diseases are notoriously difficult to diagnose, as they are highly complex conditions featuring several layers of symptoms that are not always outwardly apparent. There is currently no tool or single test on the market that is able to reliably diagnose (or even distinguish between} diseases such as Alzheimer's and Parkinson's. Embodiments of the present systems and methods may provide neurologists with a powerful new tool to assist with the diagnostic process and management. Early detection can mean the difference between extended life and early death for millions of people, especially for those with neurodegenerative conditions. Earlier treatment is typically more effective.

In embodiments, the BCCS 404 may initially be a specialized device for detecting neurological disorders and tracking their progression. In embodiments, the system may become trained to recognize disease patterns and biomarkers for a number of conditions not formerly considered neurological. Embodiments of the BCCS 404 may develop into a more general-purpose tool, capable of reaching into an even wider clinical market. Once neural scan data can be shown to provide sufficient actionable intelligence, they will appear at every hospital bedside, alongside the heart monitor.

In embodiments, an implantable device for optical recording and control of neural activity may be utilized. Embodiments may be termed the Brain Co-Processor (BCP). BCP 400 may consist of a microfabricated carbon nanotube (CNT) neural interface, a processor unit for radio transmission and communicating input and output (I/O), a light modulation and detection silicon photonic chip, and an independent receiver system where all the processing will preside. It will be self-regulating, and perform reading and writing near real-time. Transcranial Pulse Ultrasound (TPU) may be used to adhere the CNT to the cells.

Successful implementation of BCP 400 may require local processing of information from implanted electrode arrays followed by transmission (preferably wireless) across the skull. This may be accomplished with minimal power consumption in order to prolong battery life and to avoid excessive dissipation of heat within the cranium. In embodiments, an ultra-low power neural amplifier along with circuits and algorithms may be used for compression of neural recording data.

Embodiments may employ optogenetics; a technology in which light-sensitive ion channels are expressed in target neurons allowing their activity to be controlled by light. Embodiments may include miniature implantable devices that can deliver light to precise locations deep within the brain and record electrical activity at the same target locations. The light-activated proteins channelrhodopsin-2 and halorhodopsin can be used to activate and inhibit neurons in response to light of different wavelengths. Embodiments may employ precisely-targetable fiber arrays and in vivo-optimized expression systems to enable the use of this tool in awake, behaving primates. This approach may open the door to a new generation of therapies based on light activation.

In embodiments, CNT electrode arrays may be produced on a tissue culture surface. These arrays may be used to deliver patterned stimulation to neurons in culture, in order to explore synaptic plasticity rules and neural network effects in vivo. Such a system may ultimately form the basis of a new platform for drug discovery, by allowing high-throughput screening of chemicals that modify the properties of neural networks in therapeutically useful ways. The results of the signal analysis may be utilized to enhance BCP 400 system operational function over time. Deploying offline advanced machine learning and algorithms may further the AI from the signal analysis.

In embodiments, the neural probe described here will be able to function in any cortical region available to neurosurgical intervention. In embodiments, the focus may be on Parkinson's disease (PD) and Post traumatic stress disorder (PTSD) in human subjects. In embodiments, probes may be implanted in cortical areas implicated in the pathogenesis of these disorders, such as the retrosplenial and medial prefrontal cortices in PTSD and widely distributed corticostriatal projections in PD. In embodiments, the neural probe may record from all pyramidal layers 2/3 down to layer 6. By including both the principal input layer 4, the intracollumnar projection layers, as well as the major output layers 5 and 6, the pathologies described above may be monitored at an unprecedented resolution, necessary for effective treatment.

In embodiments, the BCCS 404 may use a wearable sensor system that captures movement, speech, and EEG. The BCCS 404 may be the guidance and navigation system for feedback. The BCCS 404 may enable a standardized platform, to be used during awake activities (and later during activities of daily life), to collect feedback in a closed loop system, enabling faster evaluation of key parameters and real time, intelligent feedback for stimulation. In embodiments, a suite of wearable sensors integrated with a smart device may offer autonomic stimulation during daily life. Optogenetic neurostimulation may be autonomously guided by analytics powered by computational algorithms, which have been developed based on Fundamental Code Unit (FCU) architecture. FCU provides extremely high rates of throughput and compression due to unary mathematics.

In embodiments, carbon nanotubes (CNT) may be used to monitor brain activity to study long-term changes in the brain as CNT is a biocompatible material. Combining traditional photolithographic thin-film techniques with origami design elements may be another way to increase density and adaptability of neuronal interfaces. Many current devices are location-specific and only fit certain regions of the brain. BCP 400, however, may be implantable anywhere in the brain. BCP 400 system will have a deeply implanted CNT patch and a subdural transceiver, which may allow reading of neurons at the surface and in 3D. CNT fibers may allow bi-directional input and output, whereas optical fibers can only transmit one way into the brain. The microchip that will be attached to the CNT patch may be a neurologically inspired architecture, such as RALA, which may enable high-speed, native (unary) processing and parallel streaming of neural recording. CNT may have great potential as new materials for electrode construction. Compared to traditional metal or glass electrodes, polymers such as CNT are flexible and highly biocompatible, and they can be made extremely thin. These properties may be especially valuable for the construction of high-density electrode arrays that can be implanted chronically in the brain. In embodiments, CNT nanowires may be used as intracortical recording electrodes. In embodiments, such electrodes may be stably implanted in the brain for long periods of time, both for research and clinical applications.

In embodiments, a CNT-based design may enable using one design feature as both recording electrode and stimulating optical fiber. An alternative recording array technical platform may be centered around a penetrating PDMS, parylene C or polymer probe that wraps around itself or a central shank. Photolithographic polymer probes have proven reliable in designs from multiple labs working on different neurophysiological models and questions. Several common materials used (such as polyimide) may also double as optical fibers for optogenetic stimulation devices, or can be folded around traditional optical fibers. Thin-film neural probes developed in the last few years already feature hundreds of electrode leads per shank, but should be expanded for more recording channels. For this reason, folding the probe to reduce its surface area and adverse impact on the brain parenchyma may be necessary to produce a probe with the specified recording lead density. These designs aim for recording from all six layers of sensory cortex simultaneously with a very high spatial resolution along the axis of the penetrating probe. The choice of materials reflect the results of studies demonstrating the impact of flexibility and density of implanted probes on CNS tissue responses.

In embodiments, optogenetic tools may be used to enable precise unary (ON/OFF) control of specific target neurons and circuits. Optical neuromodulation has many benefits over traditional electrode-based neurostimulation. In embodiments, BCP 400 may autosense neuron activity and guide the nanotube for light stimulation. This strategy will allow precision targeting in near real time.

In embodiments, BCP 400 may meaningfully interpret and respond to local neural signaling. Embodiments of algorithms may be used for transducing neuron output into digital impulse. The algorithms may be theoretically-grounded, computational models corresponding to the theory of similarity computation in Bottom-Up and Top-Down signal interaction. These neurally derived algorithms may use mathematical abstractions of the representations, transformations, and learning rules employed by the brain, which may correspond to the models derived from the data and may correspond to the general dynamic logic and mathematical framework. BCP 400 analytics may provide improved similarity estimation, generalization from a single exemplar, and recognition of more than one class of stimuli within a complex composition ("scene") given single exemplars from each class, which may enable the ability to generalize and to abstract, nonsensory (EEG, speech, movement) data. These analytics combined may enable global (brain wide) and fine detail (communication between and within cytoarchitectonic areas) reading and writing across different timescales. We will employ maximum-entropy statistical models and other custom AI filters to account for uncertainty in the data, as well as provide predictive analytical capabilities for events yet to take place.

BCP 400 may lead to the development of brain-machine interfaces that hold great promise as a new therapeutic approach to neurological diseases and injuries. An implanted prosthetic device could, for example, enable a paralyzed patient to control a computer or mechanical device directly through signals recorded from the brain, without any need for manual controls. A wireless implanted device may allow a PD patient to regain motor capacity in matters of minutes post-surgery.

Embodiments may combine these technologies with behavioral and physiological metrics to open up new horizons for the analysis of cognition. In embodiments, a similar approach may be applied to the human nervous system; potential clinical applications include the suppression of epileptic seizures, restoration of visual perception in patients with retinal degeneration, or deep brain stimulation for conditions such as Parkinson's disease.

In embodiments, a stimulus may be administered, which may be physical in nature (such as light or sound) or may be an abstract cognitive task (such as the working memory task), and simultaneous monitoring the activity of neural activity from neurons in vivo believed to response to that stimulus are the basic research method for understanding the brain mechanisms. Characterizing the relation between the stimulus and the individual or ensemble neural response and the relation among the spiking activity of the neurons in the ensemble may be provided by brain-to-digital transformation algorithm.

In embodiments, spike sorting may be utilized. Spike sorting may include identifying spikes, determining the number of neurons, and assigning each spike to the neuron produced. Spike sorting may be a prerequisite and mandatory step for analyzing the multiple analog voltage recordings. Earliest spike sorting methods were developed based on the basic strategy of matched filtering to compare the electrode waveform against a temporally sliding template. In general, matched filtering method can be used to detect isolated waveforms of known shape and amplitude in a background of white noise. The template matching based spike sorting methods has the following limitations: 1, When waveforms of more than one spike overlap which is common in multiple extracellular recordings, the accuracy of sorting will decrease; 2, Some of the noise in neural recording is produced from the spikes of other cells. It needs hand-adjustment of the thresholding parameters which is hard for large electrode array analysis.

In embodiments, is Independent Component Analysis (ICA) may be used for spike sorting. ICA is a method that was originally developed for doing blind source separation. The basic problem is to unmix independent signals that have been linearly mixed onto channels with unknown mixing weights. An assumption underlying this technique is that the unknown sources are independent of each other, which is the case under the assumption that the extracellular space is electrically homogeneous, pairs of cells are less likely to be equidistant from both electrodes. The objective is to learn the weights that best unmix all the channels to transform the mixtures back into the independent signals.

An advantage of ICA may be that the signal separation is performed on a sample by sample basis where no information about spike shape is used. For this reason, it may be possible to achieve good performance of sorting accuracy in terms of misses and false positives, especially in cases where the background noise is not stationary but fluctuate throughout trials, which is the fact based on biophysical and anatomical considerations but is ignored by most current spike sorting algorithms. One restrictive assumption of this approach is that the number of channels must equal or greater than the number of sources, which can yield promising results for multichannel recordings.

ICA as a generalization of Principle Component Analysis (PCA), which is a statistical model. The goal of ICA is to recover the latent components from observations. ICA finds a linear representation of non-Gaussian data so that the components are statistically independent, or as independent as possible. Most algorithms for ICA, directly or indirectly, minimize the mutual information between the component estimates, which corresponds to maximization of the negentropy, a measure of non-Gaussianity of the components. The exact maximization of the negentropy is difficult and computationally demanding because a correct estimation of the source densities is required. Most of the existing ICA algorithms can be viewed as approximating negentropy through some measures. Popular ICA algorithms include Infomax ICA, EASI, JADE, Natural-Gradient ICA and FastICA Algorithms.

In embodiments, a three-layer linear auto-associative network may also be used as an ICA network, as long as the outputs of the hidden layer are independent. Though ICA algorithms are mostly for separating original sources from linear mixtures, nonlinear ICA may also be modeled by using a parameterized neural network whose parameters can be determined under the criterion of independence of its outputs. Constrained ICA is a framework that incorporates additional requirements and prior information in the form of constraints into the ICA contrast function, for example the sparseness of the mixing matrix to model the sparse connectivity of the neural network. ICA for convolutive mixtures can be used to solve the spatio-temporal sources.

In embodiments, the Bayesian ICA algorithms may offer accurate estimations for the linear model parameters, in which the source distributions are modeled explicitly using a mixture of Gaussian model. Variational Bayesian may be applied to ICA to handle small datasets with high observed dimension. The Bayesian non-stationary source separation algorithm may recover non-stationary sources from noisy mixtures in the presence of non-stationary and temporally correlated mixing coefficients and source signals.

In embodiments, advanced CNT bundles (>1,000,000) and USN may be used to adhere the neurons and hardware and then extract impulse contributions from individual cells.

In embodiments, there may be no leads between the CNT patch (deep brain) and the I/O transmitter (subdural).

Figure 5:
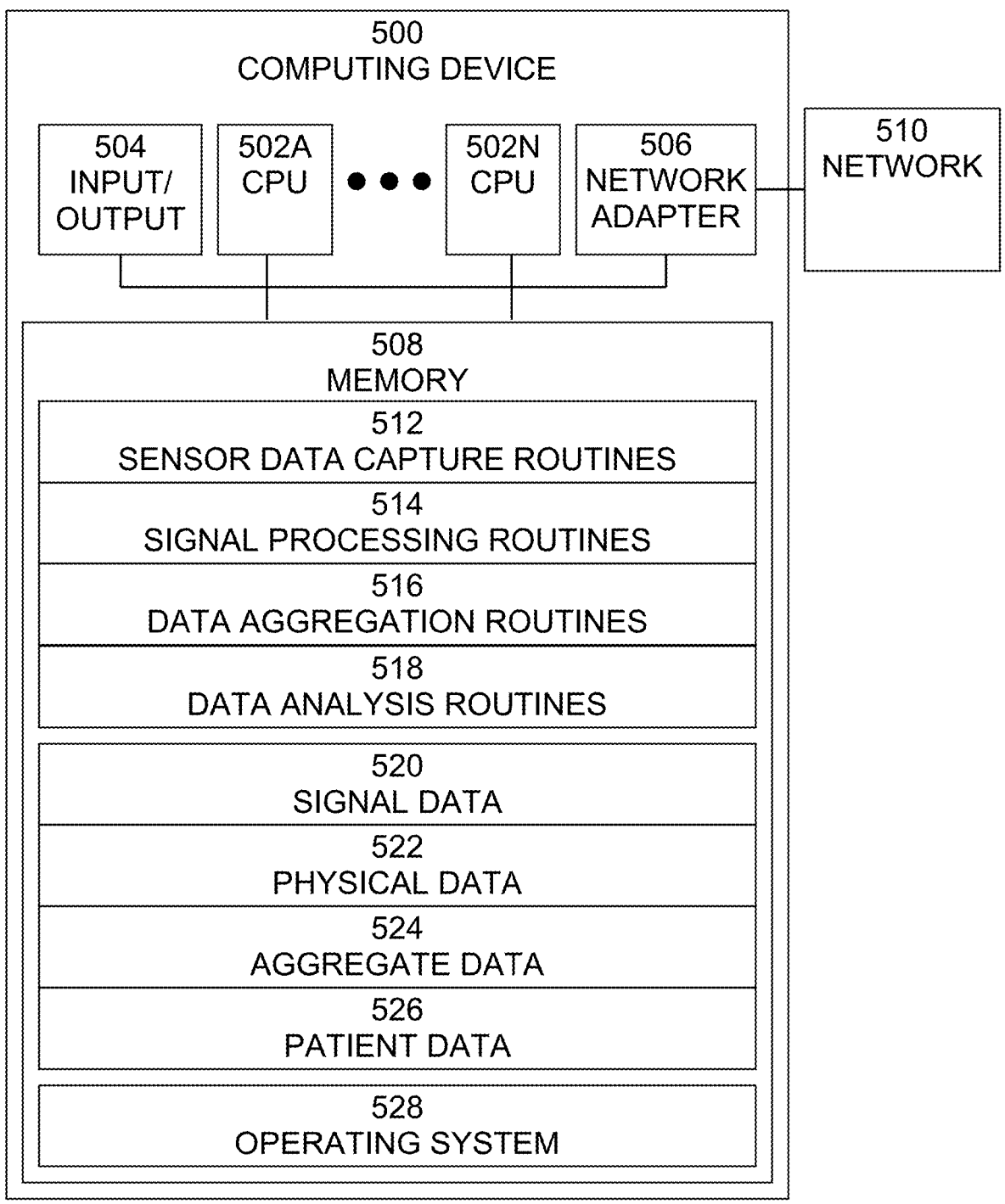
FIG. 5 is an exemplary block diagram of a computer system in which processes involved in the embodiments described herein may be implemented.

An exemplary block diagram of a computer system 500, in which processes involved in the embodiments described herein may be implemented, is shown in FIG. 5. Computer system 500 is typically a programmed general-purpose computer system, such as an embedded processor, system on a chip, personal computer, workstation, server system, and minicomputer or mainframe computer. Computer system 500 may include one or more processors (CPUs) 502A-502N, input/output circuitry 504, network adapter 506, and memory 508. CPUs 502A-502N execute program instructions in order to carry out the functions of the present invention. Typically, CPUs 502A-502N are one or more microprocessors, such as an INTEL PENTIUM® processor. FIG. 5 illustrates an embodiment in which computer system 500 is implemented as a single multi-processor computer system, in which multiple processors 502A-502N share system resources, such as memory 508, input/output circuitry 504, and network adapter 506. However, the present invention also contemplates embodiments in which computer system 500 is implemented as a plurality of networked computer systems, which may be single-processor computer systems, multi-processor computer systems, or a mix thereof.

Input/output circuitry 504 provides the capability to input data to, or output data from, computer system 500. For example, input/output circuitry may include input devices, such as keyboards, mice, touchpads, trackballs, scanners, etc., output devices, such as video adapters, monitors, printers, etc., and input/output devices, such as, modems, etc. Network adapter 506 interfaces device 500 with a network 510. Network 510 may be any public or proprietary LAN or WAN, including, but not limited to the Internet.

Memory 508 stores program instructions that are executed by, and data that are used and processed by, CPU 502 to perform the functions of computer system 500. Memory 508 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 508 may vary depending upon the function that computer system 500 is programmed to perform. One of skill in the art would recognize that routines, along with the memory contents related to those routines, may not typically be included on one system or device, but rather are typically distributed among a plurality of systems or devices, based on well-known engineering considerations. The present invention contemplates any and all such arrangements.

In the example shown in FIG. 5, memory 508 may include sensor data capture routines 512, signal processing routines 514, data aggregation routines 516, data processing routines 518, signal data 520, physical data 533, aggregate data 524, patient data 526, and operating system 528. For example, sensor data capture routines 512 may include routines to receive and process signals from sensors, such as those described above, to form signal data 520. Signal processing routines 514 may include routines to process signal data 520, as described above, to form physical data 522. Data aggregation routines 516 may include routines to process physical data 522, as described above, to generate aggregate data 524. Data processing routines 518 may include routines to process physical data 522, aggregate data 524, and/or patient data 526. Operating system 520 provides overall system functionality.

As shown in FIG. 5, the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system for monitoring brain activity comprising:
 a plurality of optical fibers, each adapted to optogenetically neurostimulate selected neuronal groups of neural tissue;
 a plurality of sensors, each adapted to monitor a physical or physiological parameter and output a signal representing the monitored physical or physiological parameter, wherein the plurality of sensors comprises a carbon nanotube patch configured to be deeply implanted, a subdural transceiver configured to read surface neurons, and a plurality of carbon nanotubes connected to the carbon nanotube patch, the plurality of carbon nanotubes configured to be in contact with the neural tissue and configured to monitor a neural tissue response of the neural tissue of pyramidal layers 4, 5, and 6;

a digital signal processor adapted to receive a plurality of signals from the plurality of sensors and to process the signals to form digital data representing the monitored physical or physiological parameter from each sensor of the plurality of sensors, and adapted to process the digital data representing the monitored physical or physiological parameter from each sensor of the plurality of sensors, to determine presence of a neurological disorder or condition.

2. The system of claim 1, wherein at least some of the plurality of sensors are selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors.

3. The system of claim 1, wherein at least some of the plurality of sensors are adapted in an earbud device and the earbud device comprises at least one component selected from a group comprising: digital storage, a controller, a pulse oximetry sensor, an TAP sensor, a kinetic power source, EEG sensors, ECG sensors, a balanced armature transducer, a microphone, a gyroscope, an accelerometer, a magnetometer, a wireless transceiver, and an optical touch sensor.

4. A computer-implemented method for monitoring brain activity comprising:

optogenetically neurostimulating selected neuronal groups of neural tissue using a plurality of optical fibers;

receiving from each of a plurality of sensors a signal representing a monitored physical or physiological parameter, wherein the plurality of sensors comprises a carbon nanotube patch configured to be deeply implanted, a subdural transceiver configured to read surface neurons, and a plurality of carbon nanotubes connected to the carbon nanotube patch, the plurality of carbon nanotubes configured to be in contact with the neural tissue and configured to monitor a neural tissue response of the neural tissue of pyramidal layers 4, 5, and 6;

processing the received signal from each of the plurality of sensors to form digital data representing the physical or physiological parameter monitored by each of the plurality of sensors; and processing the digital data representing the physical or physiological parameter monitored by each of the plurality of sensors to determine presence of a neurological disorder or condition.

5. The method of claim 4, wherein at least some of the plurality of sensors are selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors.

6. The method of claim 4, wherein at least some of the plurality of sensors are adapted in an earbud device and the earbud device comprises at least one component selected from a group comprising: digital storage, a controller, a pulse oximetry sensor, an TAP sensor, a kinetic power source, EEG sensors, ECG sensors, a balanced armature transducer, a microphone, a gyroscope, an accelerometer, a magnetometer, a wireless transceiver, and an optical touch sensor.

7. A system for monitoring brain activity, the system comprising:

a plurality of sensors, each adapted to monitor a physical or physiological parameter and output a signal representing the monitored physical or physiological parameter, wherein the plurality of sensors comprises a carbon nanotube patch configured to be deeply implanted, a subdural transceiver configured to read surface neurons, and a plurality of carbon nanotubes connected to the carbon nanotube patch, the plurality of carbon nanotubes configured to be in contact with neural tissue and configured to monitor a neural tissue response of the neural tissue of pyramidal layers 4, 5, and 6; and a processor, a memory accessible by the processor, and computer program instructions stored in the memory and executable by the processor to perform:

optogenetically neurostimulating selected neuronal groups of the neural tissue using a plurality of optical fibers;

receiving from each of the plurality of sensors the signal representing the monitored physical or physiological parameter;

processing the received signal from each of the plurality of sensors to form digital data representing the physical or physiological parameter monitored by each of the plurality of sensors; and processing the digital data representing the physical or physiological parameter monitored by each of the plurality of sensors to determine presence of a neurological disorder or condition.

8. The system of claim 7, wherein at least some of the plurality of sensors are selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors.

9. The system of claim 7, wherein at least some of the plurality of sensors are adapted in an earbud device and the earbud device comprises at least one component selected from a group comprising: digital storage, a controller, a pulse oximetry sensor, an TAP sensor, a kinetic power source, EEG sensors, ECG sensors, a balanced armature transducer, a microphone, a gyroscope, an accelerometer, a magnetometer, a wireless transceiver, and an optical touch sensor.

* * * * *